United States Patent [19]

Alpers et al.

[11] 4,098,826
[45] Jul. 4, 1978

[54] PROCESS FOR THE PREPARATION OF FORMALDEHYDE

[75] Inventors: Heinz-Jürgen Alpers; Heinz Jörg Rosenbaum, both of Krefeld, Germany

[73] Assignee: Bayer Aktiengesellschaft, Leverkusen, Germany

[21] Appl. No.: 731,488

[22] Filed: Oct. 12, 1976

[30] Foreign Application Priority Data

Oct. 31, 1975 [DE] Fed. Rep. of Germany ....... 2548908

[51] Int. Cl.$^2$ ............................................. C07C 45/16
[52] U.S. Cl. ................................. 260/603 C; 260/606
[58] Field of Search ................... 260/603 C, 606, 601, 260/604 R, 601 R

[56] References Cited

U.S. PATENT DOCUMENTS

| | | | |
|---|---|---|---|
| 2,444,924 | 7/1948 | Farkas et al. | 260/603 C |
| 3,080,426 | 3/1963 | Kirshenbaum et al. | 260/603 C |
| 3,928,461 | 12/1975 | Diem | 260/603 C |

OTHER PUBLICATIONS

Hayman et al., J.A.C.S. vol. 84, No. 12, 1962, pp. 2323-2326.

*Primary Examiner*—Robert Gerstl
*Assistant Examiner*—Werren B. Lone
*Attorney, Agent, or Firm*—Burgess, Dinklage & Sprung

[57] ABSTRACT

An improvement in the process for the preparation of formaldehyde by oxidative dehydrogenation of methanol with air in the presence of a silver catalyst at an elevated temperature wherein into the reactor in which the methanol is charged there is passed a stream of gas containing a halogen or halogen compound.

14 Claims, No Drawings

PROCESS FOR THE PREPARATION OF FORMALDEHYDE

The invention relates to a process for the preparation of formaldehyde by oxidative dehydrogenation of methanol with air in the presence of a silver catalyst at elevated temperature, in which process the stream of gas entering into the reactor contains halogens or halogen compounds.

It is known to prepare formaldehyde by partial oxidation and dehydrogenation of methanol in the presence of metallic catalysts, such as platinum, silver or copper, using a less than equivalent amount of air (Ullmanns Enzyklopädie der technischen Chemie (Ullmann's Encyclopaedia of Industrial Chemistry), 3rd edition, Volume 7, pages 659 et seq. (1956)). At present, it is mainly silver catalysts, especially a loose mass of silver crystals, which are used and, in order to raise the upper explosive limit of the air/methanol mixture, steam is preferably added.

Usually, a water-containing methanol is vaporised and this vapour is passed, as a mixture with air, over the catalyst.

The methanol is oxidised and dehydrogenated in accordance with the equations $$CH_3OH + \tfrac{1}{2} O_2 \rightarrow CH_2O + H_2O \qquad 1.$$

$$CH_3OH \rightarrow CH_2O + H_2 \qquad 2.$$

The catalyst is set to a temperature of 500° to 750° C by the highly exothermic reaction (1) and by partial combustion of the hydrogen formed by reaction (2). This temperature is controlled by the amount of air and is slowly raised from 500° to 750° C when the activity of the catalyst is decreasing.

After the reaction over the catalyst, the reaction gas essentially consists of $N_2$, $H_2O$, $H_2$, $CO_2$, $CO$ and unconverted methanol, in addition to formaldehyde.

Since formaldehyde is unstable above 400° C and decomposes to give carbon monoxide and hydrogen (loc. cit., page 658), the reaction gas is cooled as rapidly as possible and formaldehyde is then washed out with water in an absorption system, a formaldehyde solution being formed. Unconverted methanol also dissolves in water, whilst the other constituents of the reaction gas, such as $N_2$, $H_2$, $CO_2$ and $CO$, are obtained as off-gas.

Whilst unconverted methanol can be recovered and reused, $CO_2$ and $CO$ are the essential by-products and are the cause of the losses in yield.

In the case of a typical off-gas analysis of 77.9% of $N_2$, 18.0% of $H_2$, 0.1% of $O_2$, 3.6% of $CO_2$ and 0.4% of $CO$, the losses in the form of $CO_2$ and $CO$ are about 7 mol % of the methanol employed. The industrial process is thus certainly still in need of improvement.

Furthermore, the activity of the catalyst decreases during the operating time (compare DT-AS (German Published Specification) No. 1,133,357 and DT-AS (German Published Specification) No. 2,220,655). This decrease in activity is supposed to be due in particular to impurities in the air and amongst these halogens and halogen-containing substances, such as hydrogen chloride, hydrogen fluoride, volatile halides and volatile halogen compounds, such as carbon tetrachloride, are mentioned explicitly.

Surprisingly, it has now been found that the catalyst does not lose its activity and the yield of formaldehyde from the process for the preparation of formaldehyde by oxidative dehydrogenation of methanol with air in presence of a silver catalyst at elevated temperature can be improved when the stream of gas which enters into the reactor contains halogens and/or halogen compounds.

Halogens which may be mentioned are fluorine and chlorine, but preferably bromine and iodine.

Halogen compounds which can be used in the process according to the invention are both inorganic halogen compounds and organic halogen compounds; bromine and iodine compounds are preferred.

Inorganic halogen compounds which may be mentioned are hydrogen halides, such as hydrogen fluoride, hydrogen chloride, hydrogen bromide and hydrogen iodide; and also volatile and non-volatile halides, such as iodine trichloride, ammonium iodide, phosphorus triiodide, silver bromide, silver iodide and boron trifluoride.

Organic halogen compounds which can be used are, preferably, volatile bromine and iodine compounds, especially alkyl bromides and iodides and aryl bromides and iodides, which contain up to 8 carbon atoms in the organic radical; accordingly, the corresponding benzyl halides and phenylethyl halides can also be used.

Examples of organic halogen compounds which may be mentioned are halogenoalkanes, such as methyl chloride, methyl bromide, methyl iodide, ethyl iodide, n-propyl iodide, 2-bromopropane, tert.-butyl iodide and fluorodiiodomethane; furthermore, aromatic halogenated hydrocarbons, such as chlorobenzene, bromobenzene, iodobenzene, 1-bromo-4-chlorobenzene, p-dibromobenzene, o-dibromobenzene, p-iodotoluene and 1,2,4-trichlorobenzene; but also araliphatic halogenated hydrocarbons, such as benzyl iodide, can also be used.

Of course, mixtures of halogens and/or halogen compounds can also be employed.

The halogens and halogen compounds according to the invention are added in a concentration of $10^{-6}$ to 1 mol %, and especially of $10^{-5}$ to $10^{-1}$ mol %, relative to number of moles of methanol employed.

The addition of the halogens and halogen compounds according to the invention can be effected in various ways.

Gaseous compounds are mixed in the customary manner, from a pressure vessel or using air or an inert gas as the propellant, or with the aid of a blower. Liquid compounds are vaporised, either in a small supplementary vaporiser or by heating and simultaneously passing a stream of steam or an inert gas through the compound, and metered in. Moreover, it is possible to volatilise these additives together with the water/methanol mixture.

Finally liquid and also dust-fine ground solid halogen compounds can be injected into the gas space above the silver catalyst by atomizing them, for example using compressed ar or an inert gas as the propellant.

The process according to the invention can be carried out in the customary manner; the starting material, the catalyst, the pressure and the temperature can be chosen, and varied, in the usual way and are not an essential feature of the invention.

The reaction gas can be worked up in the customary manner. The ions which arise in the reaction gas as a result of the addition of halogen or halogen compounds can be washed out, for example in the customary manner with water, and removed from the resulting aqueous solution of formaldehyde for example through an ion exchanger in a known and customary manner. For this purpose, ion exchangers can be inserted at a suitable point, for example in the stream of the aqueous solution of formaldehyde which is withdrawn or also even in the circulating stream of the formaldehyde-containing wash solution.

Unless otherwise stated, the parts indicated in the examples which follow are parts by weight.

EXAMPLE 1 (Comparison Example)

100 parts of methanol, mixed with 75 parts of water, are vaporised and passed, as a mixture with 166 parts of air, per hour over a silver catalyst. A loose mass of silver crystals, such as is described in German Auslegeschrift (German Published Specification) No. 1,285,995, is used as the catalyst. The catalyst remains at a temperature of 650° C, due to the heat of reaction. The gases, which are cooled rapidly, are washed with 75 parts of water in an absorption column. Per hour, 82 parts of formaldehyde, 186 parts of water and 4 parts of methanol are obtained as the sump product from the absorber. This corresponds to a yield of 87.5 mol % of formaldehyde, relative to the methanol employed.

At the same time, 146 parts of off-gas of the following composition: 18% by volume of $H_2$, 0.1% by volume of $O_2$, 3.6% by volume of $CO_2$, 0.4% by volume of CO and 77.9% by volume of $N_2$ are formed.

EXAMPLE 2

The process is carried out under the same conditions as in Example 1 but 0.004 part of methyl iodide in the vapour form is added, per hour, upstream of the catalyst. Per hour, 86.8 parts of formaldehyde, 192 parts of water and 2.3 parts of methanol are now obtained as the sump product.

This signifies a yield of 92.6 mol % of formaldehyde, relative to the methanol employed; the increase in the yield is 5 percentage points.

The formalin solution obtained is freed from the iodide ions in a known manner by means of an anion exchanger and is then suitable direct for further processing. At the same time, 136 parts of off-gas having the composition: 17% by volume of $H_2$, 2.5% by volume of $CO_2$, 0.3% by volume of CO, 0.15% by volume of $O_2$ and 79.95% by volume of $N_2$ are formed.

EXAMPLES 3 to 8

The procedure in Examples 3 to 8 was as in Example 2. except that methylene chloride, methylene chloride together with carbon tetrachloride and chlorobenzene, and also isopropyl bromide, iodine and hydrogen iodide were employed in place of methyl iodide in the vapour form.

The amounts, in parts, of these halogen compounds which were added per hour, the composition of the off-gas, in % by volume, the amounts of formaldehyde and unconverted methanol obtained and the yields, relative to converted methanol and to the methanol employed, in mol %, are given in Table I which follows.

EXAMPLE 9

The reaction was carried out in the same way as described in Example 1, except that 0.04 part of dust-fine silver iodide was blown onto the catalyst per hour by means of a stream of nitrogen. The results obtained are also given in Table I.

Table 1

| No. | Parts of halogen compounds | Off-gas analysis (% by volume) | | | | | Amount obtained/ hour (parts) | | Yield (mol %) relative to | | Increase in yield (difference, mol %) |
|---|---|---|---|---|---|---|---|---|---|---|---|
| | | $N_2$ | $H_2$ | $CO_2$ | CO | $O_2$ | $CH_2O$ | $CH_3OH$ | converted methanol | methanol employed | |
| 1 | — | 77.9 | 18 | 3.6 | 0.4 | 0.1 | 82.1 | 3.8 | 91.1 | 87.6 | — |
| 2 | 0.004 $CH_3I$ | 79.95 | 17 | 2.5 | 0.3 | 0.15 | 86.8 | 2.3 | 94.8 | 92.6 | 5 |
| 3 | 0.5 $CH_2Cl_2$ | 81.6 | 15.3 | 2.7 | 0.3 | 0.1 | 82.8 | 6.3 | 94.3 | 88.3 | 0.7 |
| 4 | 1 $CH_2Cl_2$ | 84.5 | 13.2 | 1.8 | 0.4 | 0.1 | 83.1 | 7.5 | 95.9 | 88.6 | 1.0 |
| 5 | 0.02 $CH_2Cl_2$ +0.02 $CCl_4$ +0.02 chlorobenzene | 78.8 | 17.4 | 3.4 | 0.3 | 0.1 | 83.2 | 4.4 | 92.8 | 88.7 | 1.1 |
| 6 | 0.05 isopropyl bromide | 81.8 | 16 | 1.8 | 0.3 | 0.1 | 88.5 | 1.9 | 96.2 | 94.4 | 6.8 |
| 7 | 0.003 iodine | 80.0 | 17.0 | 2.6 | 0.3 | 0.1 | 86.6 | 2.4 | 94.6 | 92.3 | 4.7 |
| 8 | 0.01 HI | 80.6 | 16.8 | 2.2 | 0.3 | 0.1 | 87.1 | 1.9 | 95.5 | 93.4 | 5.8 |
| 9 | 0.04 AgI | 85.0 | 12.5 | 2.1 | 0.4 | 0.04 | 86.3 | 3.3 | 95.3 | 92.1 | 4.5 |

What is claimed is:

1. In a vapor phase process for the preparation of formaldehyde by oxidative dehydrogenation of methanol at 500° to 750° C with air in the presence of a silver catalyst at an elevated temperature, the improvement which comprises feeding a stream of gas into the reaction mixture containing a halogen or halogen compound, said halogen compound selected from the group consisting of, a hydrogen halide, an inorganic halide selected from the group consisting of ammonium iodide, phosphorus triiodide, silver bromide, silver iodide and boron trifluoride, a halogen alkane with up to 8 carbon atoms in the alkyl group, an aromatic halogenated hydrocarbon with up to 8 carbon atoms where the aromatic nucleus is a phenyl ring, or an araliphatic halogenated hydrocarbon with up to 8 carbon atoms in the aliphatic group where the aromatic group contains 6 carbon atoms.

2. A process according to claim 1 wherein the halogen or halogen compound is bromine, iodine, a bromine compound or an iodine compound.

3. A process according to claim 1 wherein the halogen or halogen compound is introduced into the reaction mixture in an amount of $10^{-6}$ to 1 mole percent, based upon the amount of methanol employed.

4. A process according to claim 3 wherein the amount of halogen or halogen compound introduced into the reaction mixture is $10^{-5}$ to $10^{-1}$ mole percent, based upon the amount of methanol employed.

5. A process according to claim 1 wherein a halogen compound is employed and the halogen compound is selected from the group consisting of an alkyl bromide, an alkyl iodide, an aryl bromide, an aryl iodide, a benzyl halide, and a phenylethyl halide.

6. A process according to claim 1 wherein an organic halogen compound is introduced into the reaction mixture and the organic halogen compound is selected from the group consisting of methyl chloride, methyl bromide, methyl iodide, ethyl iodide, n-propyl iodide, 2- bromopropane, tert.-butyl iodide, fluorodiiodomethane, chlorobenzene, bromobenzene, iodobenzene, 1-bromo-4-chlorobenzene, p-dibromobenzene, odibromobenzene, p-iototoluene, 1,2,4-trichlorobenzene, and benzyl iodide.

7. A process according to claim 1 wherein a halogen compound is employed which is methyl iodide.

8. A process according to claim 1 wherein a halogen compound is employed which is methylene chloride.

9. A process according to claim 8 wherein said methylene chloride is in admixture with carbon tetrachloride.

10. A process according to claim 8 wherein said methylene chloride is in admixture with chlorobenzene.

11. A process according to claim 1 wherein a halogen compound is employed which is silver iodide.

12. A process according to claim 1 wherein a halogen compound is employed which is isopropyl bromide.

13. A process according to claim 1 wherein a halogen compound is employed which is hydrogen iodide.

14. A process according to claim 1 wherein halogen is employed which is iodine.

* * * * *